Figure 1A:
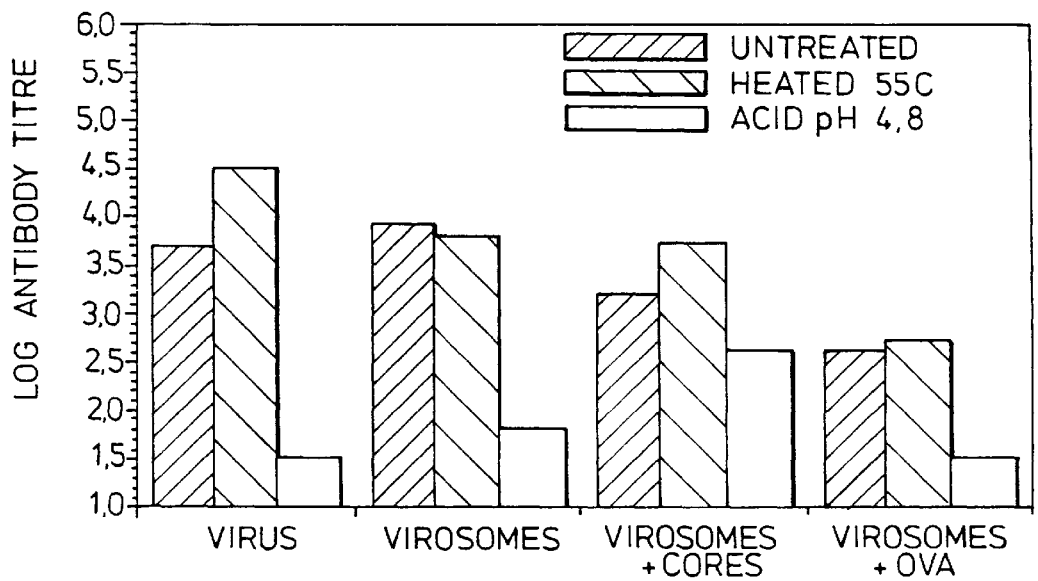

United States Patent [19]
Ford

[11] Patent Number: 5,985,318
[45] Date of Patent: Nov. 16, 1999

[54] FUSOGENIC LIPOSOMES THAT ARE FREE OF ACTIVE NEURAMINIDASE

[75] Inventor: Martin James Ford, Beckenham, United Kingdom

[73] Assignee: Burroughs Wellcome Co., Research Triangle Park, N.C.

[21] Appl. No.: 08/406,101

[22] Filed: Mar. 16, 1995

Related U.S. Application Data

[63] Continuation of application No. 07/974,589, Feb. 22, 1993, abandoned.

[30] Foreign Application Priority Data

Aug. 24, 1990 [GB] United Kingdom .................... 9018690

[51] Int. Cl.$^6$ ......................... A61K 9/127; A61K 39/385; A61K 39/12; C12N 7/04
[52] U.S. Cl. ....................... 424/450; 435/236; 424/193.1; 424/204.1; 424/206.1
[58] Field of Search ................................ 424/450, 193.1, 424/204.1, 206.1; 435/236

[56] References Cited

U.S. PATENT DOCUMENTS 4,235,877 11/1980 Fullerton ................................ 424/450

FOREIGN PATENT DOCUMENTS 011549 7/1979 European Pat. Off. .
356339 8/1989 European Pat. Off. .

OTHER PUBLICATIONS

Hackett C, Taylor P, Askonas B; Stimulation of cytotoxic T cells by liposomes containing influenza virus or its components Immunology 29: 255–262, 1983.

Yewdell J, Bennink J, Hosaka Y; Cells process exogenous proteins for recognition by cytotoxic T lymphocytes Science 239: 637–640, 1988.

Martindale: The Extra Pharmacopoeia, Twenty–nineth Edition, James E.F. Reynolds, Editor, London, The Pharmaceutical Press, pp. 1165–1166 (1989).

Schulman et al, Protective Effects of Specific Immunity to Viral Neuraminidase on Influenza Virus Infection of Mice, Journal of Virology 2(8):77–786 (1968).

Couch et al, "Induction of Partial Immunity to Influenza by a Neuraminidase–specific Vaccine", The Journal of Infectious Diseases 129(4):411–420 (1974).

Beutner et al, "Evaluation of a Neuraminidase–Specific Influenza A Virus Vaccine in Children: Antibody Responses and Effects on Two Successive Outbreaks of Natural Infection", The Journal of Infectious Diseases 140(6):844–850 (1979).

Primary Examiner—Jeffrey Stucker
Assistant Examiner—Hankyel T. Park
Attorney, Agent, or Firm—Nixon & Vanderhye P.C.

[57] ABSTRACT

Liposomes which have present on their surface a polypeptide capable of binding to a mucosal cell surface of a human or animal and which are substantially free of active neuraminidase are useful as vaccines.

13 Claims, 16 Drawing Sheets

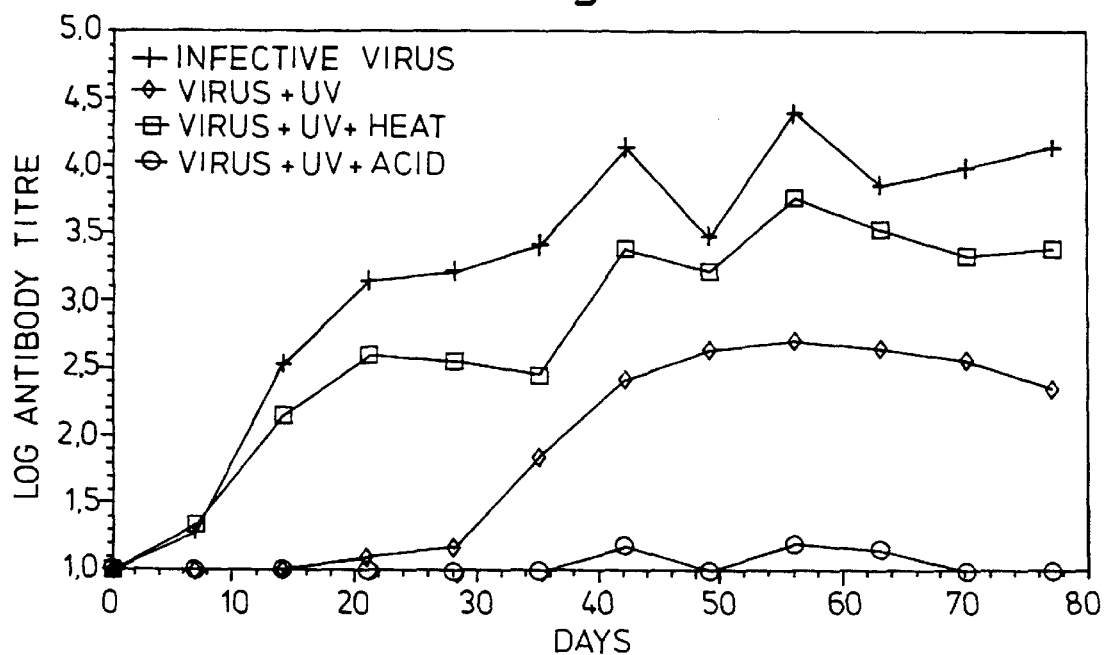
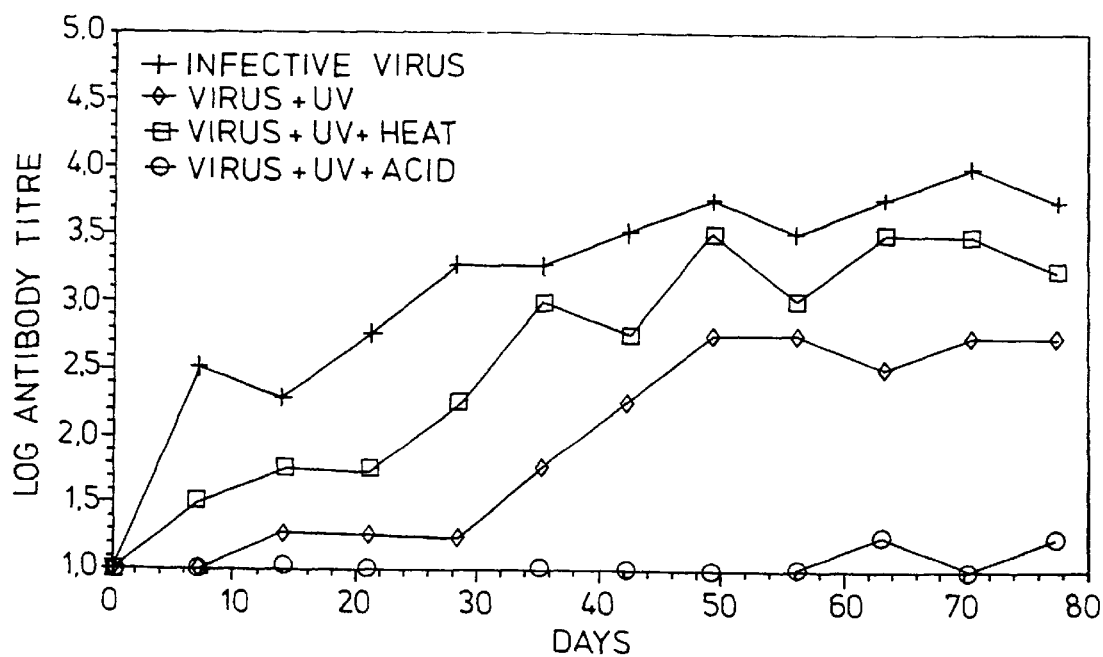

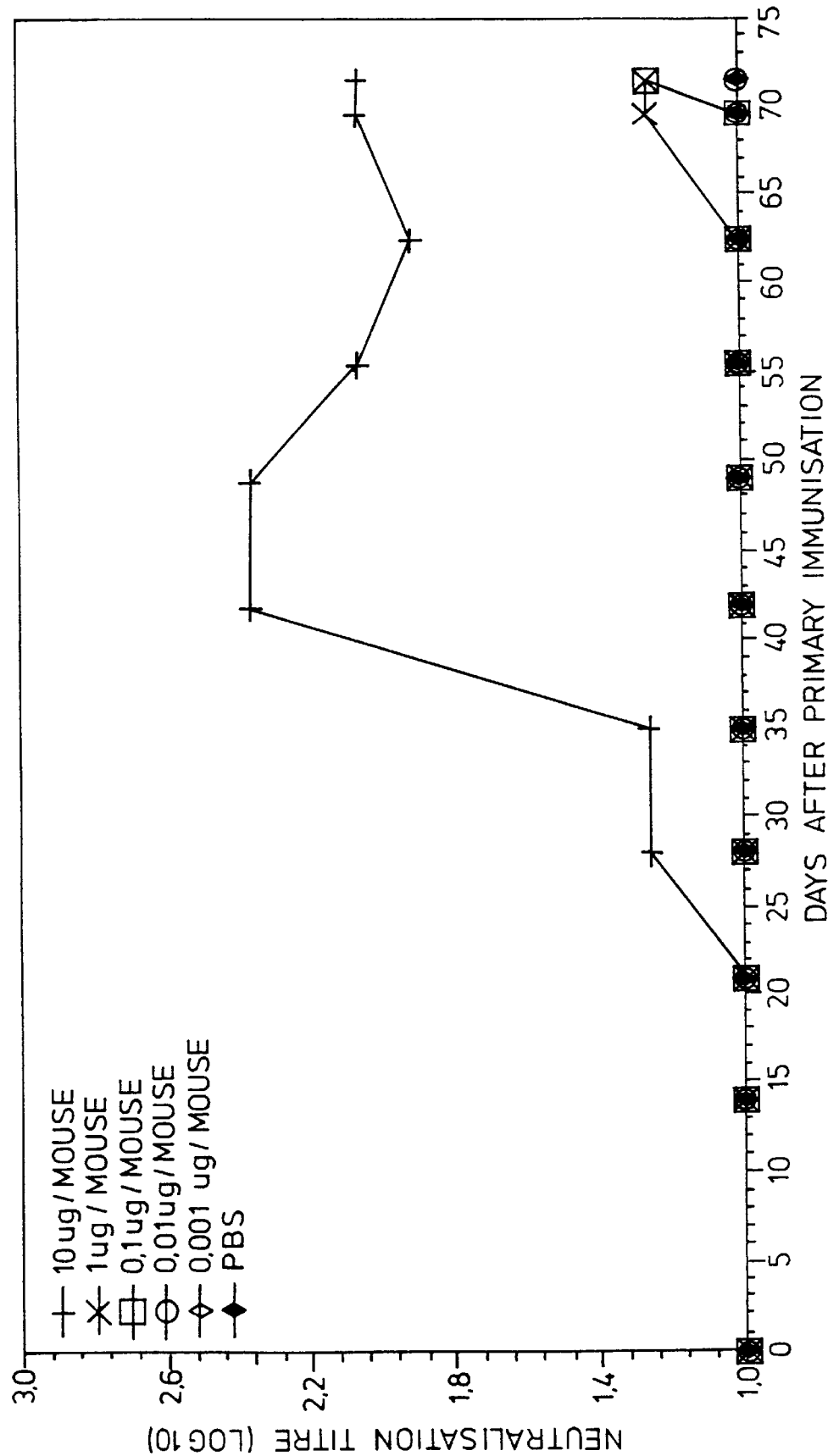

FUSOGENIC LIPOSOMES THAT ARE FREE OF ACTIVE NEURAMINIDASE

This is a continuation of application Ser. No. 07/974,589, filed Feb. 22, 1993 now abandoned.

FIELD OF THE INVENTION

This invention relates to liposomes, a process for their preparation, and pharmaceutical compositions containing them.

DESCRIPTION OF THE RELATED ART

It is known that while a variety of inactivated viruses are good immunogens they are also pyrogenic which presents a serious disadvantage To their use as vaccines. One example of this are current influenza vaccines. These are composed of whole virus and suffer from problems of pyrogenicity as well as sensitization to egg proteins. An alternative is to use influenza vaccines composed of virus sub-units but these are poorly immunogenic and stimulate poor protection compared to live infection.

Generally, the poorest responses to influenza vaccines are observed in elderly patients who are most at risk from complications and death following infection with influenza. In addition to these problems, influenza vaccines are unpopular as they are conceived to be ineffective and because of fear of injections. GB-A-1564500 discloses antigenic preparations containing a plurality of unilamellar microvesicles, otherwise known as virosomes, each microvesicle comprising a single lipid bilayer upon the exterior surface of which is bound an antigenic protein derived from a virus. GB-A-1564500 is related to two U.S. Continuation-in-Part Patents, U.S. Pat. No. 4,196,191 and U.S. Pat. No. 4,148,876. U.S. Pat. No. 4,148,876 discloses antigenic virosome preparations of the type disclosed in GB-A-1564500 in which the antigenic protein is bound by hydrophobic bonding and is a haemagglutinin and neuraminidase sub-unit of a protective surface antigen derived from a myxovirus and having a hydrophobic region.

DESCRIPTION OF THE INVENTION

We have now found that influenza virosomes which comprise reconstituted virus envelopes and which have been treated to inactivate neuraminidase are highly immunogenic when administered intranasally. Significant IgA responses were observed in the lung lavage fluid of mice immunised intranasally but not parenterally. These findings have general applicability. Accordingly, the present invention provides liposomes which have present on their surfaces a polypeptide capable of binding to a mucosal cell surface of a human or animal and which are substantially free of active neuraminidase. The liposomes are typically virosomes.

Liposomes are lipid vesicles enclosing a three-dimensional space. Envelope viruses comprise a lipid envelope. Liposomes according to the present invention may therefore be made of the lipid of an envelope virus. The virus envelope may be reconstituted after an envelope virus has been disrupted, for example by a detergent, thereby to form liposomes.

Useful liposomes may also be made of natural or synthetic phosphocholine-containing lipids having one fatty acid chain of from 12 to 20 carbon atoms and one fatty acid claim of at least 8 carbon atoms, for example 12 to 20 carbon atoms. Such lipids include dimyristoylphosphatidyl-choline, dioleoylphosphatidylcholine, dipalmitoylphosphatidylcholine, dipalmitoylphosphatidylglycerol, distearoylphosphatidylcholine, phosphatidylcholine, phosphatidylserine and sphingomyelin. Another lipid may also be included in the liposomes, for example cholesterol, which is preferably present as less than 30% w/w of the whole lipid composition. The lipids may further comprise a material to provide a positive or negative charge, such as phosphatidic acid, dicetyl phosphate, phosphatidyl serine or phosphatidyl inositol to provide a negative charge or stearyl amine or other primary amines to provide a positive charge.

The liposomes used in the present invention may be either unilamellar or multilamellar, preferably unilamellar. They are typically biodegradable. The lipid of which they are composed is generally non-antigenic. The liposomes may encapsulate a substance, for example an antibody, antigen or drug. They may therefore be used as a delivery system for the encapsulated component. The liposomes can be used as a general delivery system.

Typically the environment within the liposomes is an aqueous environment. A variety of substances can be encapsulated within the liposomes, such as peptides, proteins or adjuvants. The substance may be a substance against which it is wished to induce an immune response. Substances which may be encapsulated include antigenic subunits prepared from many types of virus such as herpes simplex virus, hepatitis A virus and hepatitis B virus. Proteins or peptides containing class 1 T-cell epitopes may be used. Encapsulation of this material within virosomes may help to generate a cytotoxic T-cell response against them.

The liposomes are preferably in a form which is suitable for intranasal administration. Preferably, therefore, the mucosal cell surface-binding polypeptide imparts on the liposomes the ability to bind to the nasal mucosa or to the mucosa of the lungs. Preferably the diameter of the liposomes is from 5 to 1000 nm, for example to 400 nm and most preferably from 20 to 100 nm.

The polypeptide capable of binding to a mucosal cell surface may be glycosylated or unglycosylated. The polypeptide may therefore be in the form of a glycoprotein. Preferably the polypeptide renders the liposomes fusogenic so that they are able to fuse with, rather simply bind to, host cell membranes. These membranes may be either the outer membrane of the membrane of endosomes following endocytosis. The polypeptide is typically a virus envelope polypeptide or is derived from a virus envelope polypeptide. All envelope viruses have a surface-binding function. The polypeptide may therefore be a polypeptide which is naturally present on the surface of an envelope virus and which provides the liposomes with the capability of binding to a cell surface. The virus may be a myxovirus such as influenza, mumps or measles virus. In particular the polypeptide may be or be derived from an influenza virus envelope protein, for example of influenza virus type A, B or C.

The polypeptide capable of binding to a cell surface may for example be a haemagglutinin. Haemagglutinin is an integral membrane glycoprotein present in myxoviruses which is commonly composed of three monomers or subunits. During infection of host cells, it serves two functions. Firstly, it attaches the virus to the cell by the binding of sialic acid residues present on cellular glycoproteins and glycolipids. Second, after internalization of virus into cellular endosomes the subsequent acidification triggers conformational changes in the haemagglutinin which lead to the fusion of viral and cellular membranes. Haemagglutinins are antigenic and stimulate the production of antibodies in hosts.

Another type of polypeptide capable of binding to a cell surface may be a bacterial adhesive protein such as the β-subunit of cholera toxin (CTB) or the heat-labile enterotoxin β-subunit of *E. coli* (LTB). This may also be used as an adjuvant in combination with haemagglutinin.

Neuraminidase is another glycoprotein which is found as an integral membrane protein in myxoviruses. This functions to cleave sialic acid residues and prevent the irreversible binding of virus to a host cell membrane by haemagglutinin. If active neuraminidase is present in the liposomes, then a significantly lower immunological response is observed. If active neuraminidase would otherwise be present in the liposomes, it must be inactivated. Neuraminidase may be inactivated by heat or by incubation with a neuraminidase inhibitor such as 2,3-dehydro-2-deoxy-N-acetylneuraminic acid (DDAN).

The present liposomes are prepared by a process which comprises forming liposomes which have present on their surfaces a polypeptide capable of binding to a mucosal cell surface of a human or animal and which are substantially free of active neuraminidase.

The polypeptide capable of binding to a cell surface may be added to the lipid materials before, during or after formation of the liposomes. Alternatively, virosomes can be prepared using the natural lipid of the envelope of an envelope virus to provide the necessary lipid component. If the polypeptide does not naturally associate with lipids it may be coupled to a fatty acid such as phosphatidylethanolamine (PE) by the use of a cross-linking agent such as succinimidyl 4-(p-maleimidophenyl)butyrate (SMPB).

Liposomes may for example be prepared by dissolving the lipid starting material in a solvent and evaporating the solvent. The lipid layer is then dispersed with aqueous saline or a buffer (if it is intended to incorporate the polypeptide into the liposomes after vesicle formation) or with an aqueous suspension of the polypeptide (if it is intended to form vesicles in the presence of the polypeptide). The dispersion is then agitated, for example by sonication. Polypeptide may then be added where it is not already incorporated in the surface of the liposomes and the vesicles again agitated.

An alternative method is to add the lipid starting material to an aqueous phase and slowly heat the mixture. It is then agitated to form liposomes. The aqueous phase may contain the polypeptide or it may be added subsequently.

A further method of preparing liposomes comprises the rapid injection of an ethanolic solution of lipid into aqueous saline or a buffer which has previously been purged with nitrogen. The resulting liposome preparation is then concentrated by ultrafiltration with rapid stirring under nitrogen at low pressure to avoid the formation of larger non-heterogeneous liposome. The ethanol may be removed from the vesicle fraction by analysis or washing with an ultrafilter. The polypeptide may be present in aqueous solution or alternatively the liposome fraction obtained after ultrafiltration may be lightly sonicated with the polypeptide.

The liposome preparations obtained in the manner described above comprise aqueous dispersions of the lipid vesicles.

If the liposomes comprise neuraminidase then this must be inactivated. This may be achieved by heating the aqueous dispersion of liposomes comprising active neuraminidase to a temperature of for example from 30 to 60° C., for example from 50 to 60° C., more preferably from 53 to 58° C. and most preferably about 55° C. The length of time required for neuraminidase inactivation will depend on the strain of virus and the temperature but is typically from 5 minutes to 5 hours, for example from 15 minutes to 3 hours. At low temperatures eg. 30° C. a longer period of heating is required, whilst at higher temperatures a shorter period is required. We have found for influenza virus that heating at 55° C. must be for 120 minutes or more, for example up to 180 minutes, in order to achieve an optimum effect. At 56° C., however, the optimal period for heating is from 6 to 10 minutes, for example about 8 minutes.

Alternatively, active neuraminidase may be deactivated by incubation of the liposomes with a neuraminidase inhibitor such as DDAN. As a further alternative active neuraminidase may be inactivated by heat or incubation with a neuraminidase inhibitor prior to incorporation into the liposomes.

A suitable way of preparing liposomes comprises:

(a) disrupting a myxovirus and removing the viral genome and internal viral protein or proteins; and (b) forming liposomes in the presence of the material remaining, especially the envelope protein or proteins; and (c) inactivating the neuraminidase present in the thus-formed liposomes.

Step (a) may be achieved be detergent solubilisation of viral particles and removal of internal viral proteins and RNA. In an alternative way of preparing liposomes, the cell surface-binding polypeptide may be prepared by a recombinant DNA methodology. It will then necessarily be provided free of neuraminidase, so liposomes substantially free of active neuraminidase are necessarily obtained.

The liposomes of the present invention may be administered in the form of a pharmaceutical or veterinary composition which additionally comprises a suitable pharmaceutically or veterinarily acceptable carrier or diluent. The compositions are suitable for administration intranasally.

The compositions are preferably provided in a sterilised form. They may take the form of an aerosol. The compositions may further comprise preservatives, stabilisers and other conventional vaccine excipients if required.

The dosage of liposomes will vary depending upon a variety of factors. These include the nature of the cell surface-binding protein, the recipient (human or animal), the vaccination schedule and the extent of adjuvanticity conferred by the preparation. In general a dose of liposomes may be administered intranasally as a single unit or as a multiplicity of a sub-dosage over a period of time. Typically the unit dose for intranasal delivery to a human is from 2 to 500 µg.

We have also found that inactivated influenza virus which is substantially free of inactive neuraminidase is highly immunogenic when administered intranasally. This finding also has general applicability. The invention therefore further provides:

an influenza virus which is not infectious and which is substantially free of active neuraminidase, for use as an influenza virus; and use of an influenza virus which is not infectious and which is substantially free of active neuraminidase in the preparation of a medicament for use as an influenza vaccine.

The influenza virus may be any influenza virus, for example type A, B or C. The virus is the virus against which it is wished to vaccinate. The neuraminidase may be inactivated by heating or specific inhibitors. An aqueous dispersion of the virus may be heated. Heating may be carried out at a temperature of for example from 30 to 60° C., more preferably from 53 to 58° C. and most preferably about 55° C.

The length of time for which heating must be conducted to ensure neuraminidase inactivation will depend upon the strain of virus and the temperature but is typically from 5 minutes to 5 hours, for example from 15 minutes to 3 hours. At low temperatures, e.g. 30° C., a longer period of heating is required than at higher temperatures. We have found that heating at 55° C. must be for 120 minutes of more, for example up to 180 minutes, in order to achieve an optimum effect. At 56° C., however, the optimal period for heating is from 6 to 10 minutes, for example 8 minutes.

The influenza virus is inactivated. In particular, viral infectivity is inactivated. This may be achieved by the heating to inactivate the neuraminidase. Typically, however, it is achieved by irradiation with ultraviolet light to provide a fail-safe inactivation procedure. This may be carried out before, simultaneously with or after treatment to inactivate the neuraminidase. Irradiation is carried out for at least 5 minutes, for example for from 5 to 60 minutes, at 400 $\mu W/cm^2$ at a short wavelength, for example from 240 to 250 nm. The ultraviolet-inactivated, heated virus is grown in the allantoic fluid of embryonated hens eggs, for 2–3 days, recovered and purified on sucrose gradients.

The inactivated influenza virus substantially free of active neuraminidase is administered in the form of a pharmaceutical composition which additionally comprises a suitable pharmaceutically acceptable carrier or diluent. The compositions are suitable for administration intranasally.

The compositions are preferably provided in a sterilised form. They may take the form of an aerosol. The compositions may further comprise preservatives, stabilisers and other conventional vaccine excipients if required.

The dosage of inactivated virus will vary depending upon a variety of factors. An effective amount of the inactivated influenza virus substantially free from active neuraminadase is administered to a person in need of vaccination, in particular in need of vaccination against the said virus. Factors which need to be taken into account in assessing dosage include the age of the recipient, the vaccination schedule and the extent of adjuvanticity conferred by the preparation. In general a dose may be administered intranasally as a single unit or as a multiplicity of a sub-dosage over a period of time. Typically the unit dose for intranasal delivery is from 2 to 500 $\mu g$.

The vaccines of the invention exhibit advantages over current influenza vaccines. These include immunogenicity, the convenience of intranasal administration and the production of local mucosal immunity.

The invention will now be further illustrated by means of the following Example.

BRIEF DESCRIPTION OF THE DRAWINGS

FIG. 1A shows the ELISA titres against X31 influenza virus in sera from Balb/c mice immunised intranasally (i.n.) with heated and acid-treated virosomes or virus;

FIG. 1B shows the ELISA titres against denatured virus in sera from mice immunised i.n. with heated and acid-treated virosomes or virus;

FIG. 1C shows the neutralisation titres of sera from mice immunised i.n. with heated and acid-treated virosomes or virus;

FIG. 1D shows the HAI titres against virus in sera from mice immunised i.n. with heated and acid-treated virosomes or virus;

FIG. 2A shows the ELISA titres against virus in sera from mice immunised i.n. with heated and acid-treated virus;

FIG. 2B shows the neutralisation titres against virus in sera from mice immunised i.n. with heated and acid-treated virus;

FIG. 3A shows the ELISA titres against virus in sera from mice immunised i.n. with heated and acid-treated virosomes;

FIG. 3B shows the neutralisation titres against virus in sera from mice immunised i.n. with heated and acid-treated virosomes;

FIG. 4A shows the ELISA titres against virus in sera from mice immunised i.n. with heated and acid-treated virosomes encapsulating the internal proteins and RNA (“virosome-cores”);

FIG. 4B shows the neutralisation titres against virus in sera from mice immunised i.n. with heated and acid-treated virosome-cores;

FIG. 5A shows the ELISA titres against virus in sera from mice immunised i.n. with heated and acid-treated virosomes encapsulating ovalbumin (“ova-virosomes”);

FIG. 5B shows the neutralisation titres against virus in sera from mice immunised i.n. with heated and acid-treated ova-virosomes;

FIG. 6A shows the individual ELISA titres against virus in sera (2 days post-challenge bleed) from mice immunised i.n. with heated and acid-treated virus;

FIG. 6B shows the individual neutralisation titres against virus in sera (2 days post-challenge bleed) from mice immunised i.n. with heated and acid-treated virus;

FIG. 7A shows the individual ELISA titres against virus in sera (2 days post-challenge bleed) from mice immunised i.n. with heated and acid-treated virosomes;

FIG. 7B shows the individual neutralisation titres against virus in sera (2 days post-challenge bleed) from mice immunised i.n. with heated and acid-treated virosomes;

FIG. 8A shows the individual ELISA titres against virus in sera (2 days post-challenge bleed) from mice immunised i.n. with heated and acid-treated virosome cores;

FIG. 8B shows the individual neutralisation titres against virus in sera (2 days post-challenge bleed) from mice immunised i.n. with heated/acid-treated virosome-cores;

FIG. 9A shows the individual ELISA titres against virus in sera (2 days post-challenge bleed) from mice immunised i.n. with heated and acid-treated ova-virosomes;

FIG. 9B shows the individual neutralisation titres against virus in sera (2 days post-challenge bleed) from mice immunised i.n. with heated/acid-treated ova-virosomes;

FIG. 10A shows ELISA titres showing the effect of heating on the immunogenicity of virosomes administered i.n.;

FIG. 10B shows the neutralisation titres showing the effect of heating on the immunogenicity of virosomes administered i.n.;

FIG. 11 compares the anti-virus and neutralising antibody response following immunisation with heated virosomes.

FIG. 12A shows the effect of heating at 55° C. on the immunogenicity of virosomes administered i.n.;

FIG. 12B shows the effect of heating at 55° C. on the immunogenicity of virosomes administered i.n.;

FIG. 13 shows the effect of pre-treating virosomes or mice with gangliosides on the immunogenicity of virosomes given i.n.;

FIG. 14A shows the ELISA results of sera from mice immunised i.n. on days 0 and 43 with different doses of influenza virosomes; and FIG. 14B shows the neutralisation results of sera from mice immunised i.n. on days 0 and 43 with different doses of influenza virosomes.

EXAMPLE

1. METHODS

Preparation of virosomes

The procedure for making the reconstituted virus envelopes was similar to that described by Metsikko et al. (EMBO J. 5, 3429–3435, 1986) and Stegmann et al. (EMBO J. 6, 2651–2659, 1987). A pellet of X31 influenza virus (5 mg) was solubilised in 0.7 ml of 100 mM octaethyleneglycol monododecylether ($C_{12}E_8$) in dialysis buffer (145 mM NaCl, 5 mM Hepes, pH 7.4) for 20 min at room temperature. The mixture was centrifuged at 170,000 g from 30 min to remove the internal proteins and RNA. 0.56 ml of the supernatant was added to 160 mg of wet Bio-Beads SM-2 and shaken on a rotating table (approx. 400 rpm) for 1 hour at room temperature. The supernatant was removed from the beads with a 23 g needle attached to a 1 ml syringe and added to 80 mg of wet Bio-Beads SM-2 and shaken on a rotating table (approximately 500–600 rpm) for 8 min yielding a turbid suspension. The supernatant was removed with a 23 g needle and syringe. The virosomes were separated from unincorporated protein by discontinuous sucrose gradients (40%/5% or 40%/20%/5%) spun at 170,000 g for 90 min. The morphology of the virosomes was analysed by electron microscopy using negative staining with phosphotungstate.

Virosomes containing encapsulated proteins, e.g. ovalbumin (Virosomes+ova), were made as described above except that 100 µl of 200 mg/ml ovalbumin was added prior to adding the SM-2 beads. Virosomes-cores were made as described above except that the interal proteins and RNA were not removed by centrifugation.

ELISA assays

Anti-virus antibodies in the serum from vaccinated mice were measured by ELISA (enzyme-linked immunoadsorbent assay). The virus antigen was diluted in carbonate coating buffer pH 9.5: 1/50 dilution of allantoic fluid from hens eggs inoculated with virus or 1 µg/ml of purified egg-grown virus. Microtitre plates were coated with antigen and left at 37° C. for 1 hour and then overnight at 4° C. After washing the plates 3 times in 0.05% Tween 20 in PBS 100$M^1$ of 1% BSA was added and left at 37° C. for 1 hour to block the plates. The antisera to be tested was diluted down or across the plate in doubling or half log dilutions in 1% BSA in PBS and left at 4° C. overnight. The plates were washed with Tween/PBS before adding the enzyme-conjugated second antibody at 1/500–1/1000 in 1% BSA in PBS. The plates were left at 37° C. for 2 hours and washed in Tween/PBS. The substrate, o-phenylenediamine dihydrochloride (OPD) (10 mg/100 ml) in citrate buffer with 0.01% $H_2O_2$ was added to the plates and the reaction stopped in $H_2SO_4$. The plates were read on a microplate reader at 492 nm. The titres were end point titres determined by taking the titre at which the OD value was equal to the mean OD value obtained with 1/10 dilution of control normal sera plus 2 standard deviations.

In Vitro Neutralisation Assay

We have established a microtitre plate-based neutralisation assay on MDCK cells. Serial dilutions of antibody were incubated with 2 logs of virus for 1 hour at 37° C. These were transferred to microtitre plates with 70–90% confluent MDCK cells in MEM media without serum. After incubation at 37° C. for 1 hour the supernatant was removed and fresh MEM added with 10 µg/ml trypsin. The plates were stained after 48–72 hours and the neutralisation titres read by eye.

HAI—Haemagglutination inhibition assay

Haemagglutination and haemagglutination inhibition assays were performed as described by Fazekas de St. Groth and Webster, (J. Exp. Med. 124; 331–345, 1966).

Experiments

Experiments were carried out as follows, referring to the Figures:

FIG. 1

Dose—5 µg of X31 virus/virosomes per mouse in 30 µl volume given i.n.

All virosomes were uv. inactivated for 5 min (400 µW/cm²)
Heating—heating carried out at 55° C. for 20 min.
Acid treatment—1/100th volume of 3M acetate buffer pH 4.8 was added to the virosomes. These were left at 37° C. for 15 min before neutralising the acid with 1M Tris pH 7.5.
Second immunization—6 weeks
Bleed tested—12 weeks

FIGS. 2–5

Dose—5 µg of X31 virus/virosomes per mouse in 30 µl volume given i.n.
Virosomes were uv inactivated for 5 min (400 µW/cm²)
Heating—heating carried out at 55° C. for 20 min.
Acid treatment—1/100th volume of 3M acetate buffer pH 4.8 was added to the virosomes. These were left at 37° C. for 15 min before neutralising the acid with 1M Tris pH 7.5.
Second immunization—6 weeks

FIGS 6–9

Dose—5 µg of X31 virus/virosomes per mouse in 30 µl volume given i.n.
Virosomes were uv inactivated for 5 min (400 µW/cm²)
Heating—heating carried out at 55° C. for 20 min.
Acid treatment—1/100th volume of 3M acetate buffer pH 4.8 was added to the virosomes. These were left at 37° C. for 15 min before neutralising the acid with 1M Tris pH 7.5.
Second immunization—6 weeks
Bleed tested—12 weeks

FIG. 10

Dose—3 µg of X31 virosomes per mouse in 30 µl volume given i.n.
Virosomes were uv inactivated for 5 min (400 µW/cm²)
Heating—heating carried out at 55° C. for specified times.
Second immunization—6 weeks

FIG. 11

Dose—3 µg of X31 virosomes per mouse in 30 µl volume given i.n.
Virosomes were uv inactivated for 5 min (400 µW/cm²)
Heating—heating carried out at 55° C. for specified times.
Second immunization—6 weeks
Bleed tested—8 weeks

FIG. 12

Dose—3 µg of X31 virosomes per mouse in 30 µl volume given i.n.
Virosomes were uv inactivated for 5 min (400 µW/cm²)
Heating—heating carried out at 55° C. for specified times.
Second immunization—6 weeks
Bleed tested—12 weeks

FIG. 13 preincubation with gangliosides and antibody
The virosomes were dialysed against Hepes buffer (145 mM NaCl, 5 mM Hepes pH 7.4 plus 3 mM EDTA). These 30 virosomes were heated at 55° C. for 1 hour. Dose—3 µg/mouse in 30 µl volume.
Incubation with gangliosides—Virosomes were incubated at 37° C. for 1 hour and then overnight at 4° C. with a 12 Molar excess of gangliosides to viral haemagglutinin.
Pretreatment of mice with gangliosides—100 Molar excess of gangliosides to viral haemagglutinin.
Incubation with antibody—20 µg of virosomes were incubated in 40 µg of purified HC2 antibody or 20 µg HC2 Fab fragments for 2 hours at 37° C.

Administration of virosomes with CTB

Figure 14A:
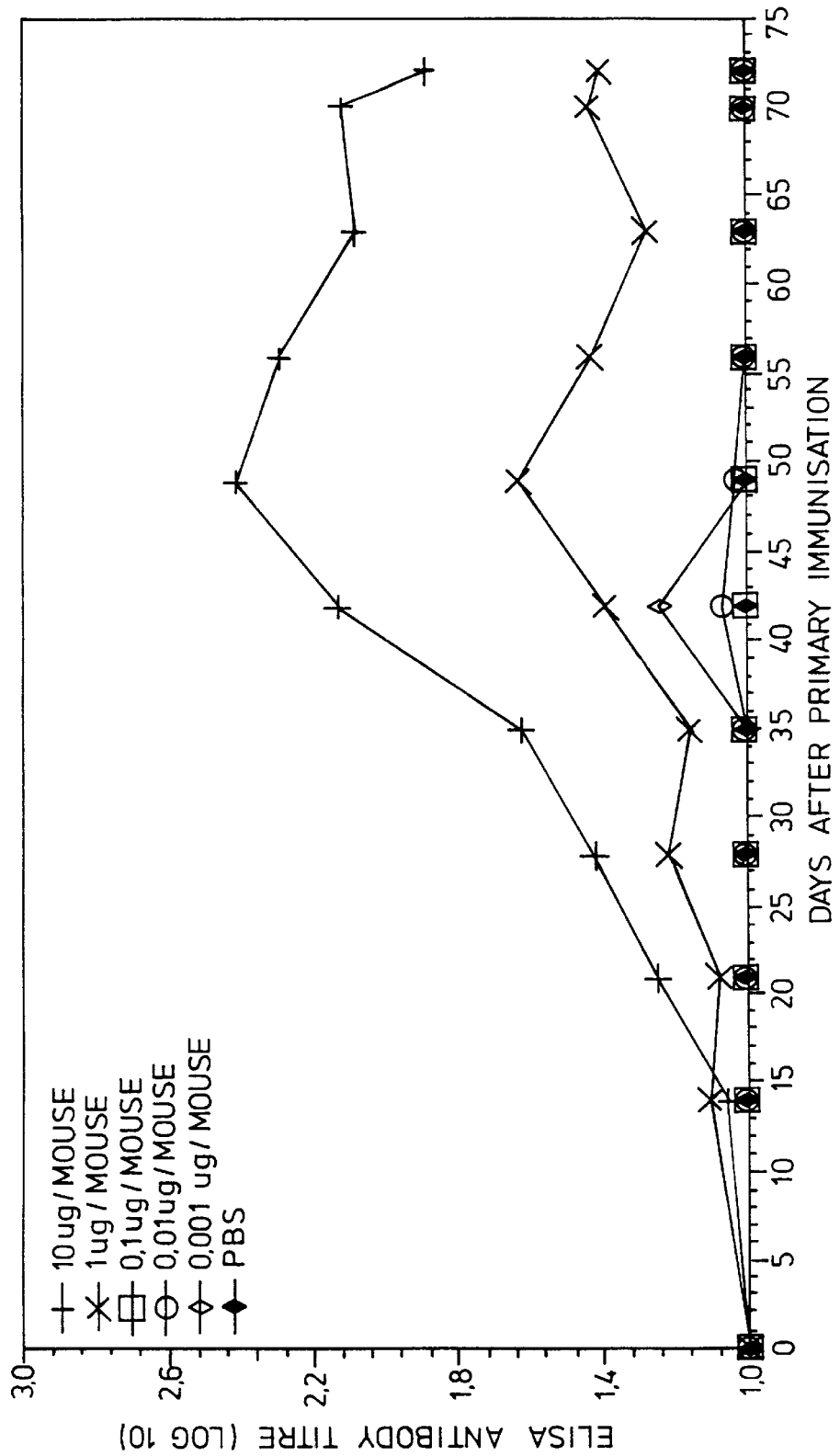

2 μg of CTB (B-subunit of cholera toxin) was given together with 3 μg of virosomes to each mouse.
Second immunization—6 weeks
Bleed tested—12 weeks
Treatment with DDAN 20 μg of virosomes were incubated with 1 mM DDAN for 1 hour at 37° C. and then at 4° C. overnight.
dose per mouse=3 μg in 30 μl volume i.n.
Second immunization—6 weeks
Bleed tested—12 weeks
FIG. 14 (Dose response)

Dose—variable dose of X31 virosomes in 30 μl volume given i.n.
Virosomes were uv inactivated for 5 min (400 μW/cm$^2$)
Heating—heating carried out at 55° C. for specified times.
Second immunization—6 weeks

2. RESULTS

Effect of acid-treatment on the immunogenicity of virus and virosomes

Figure 1B:
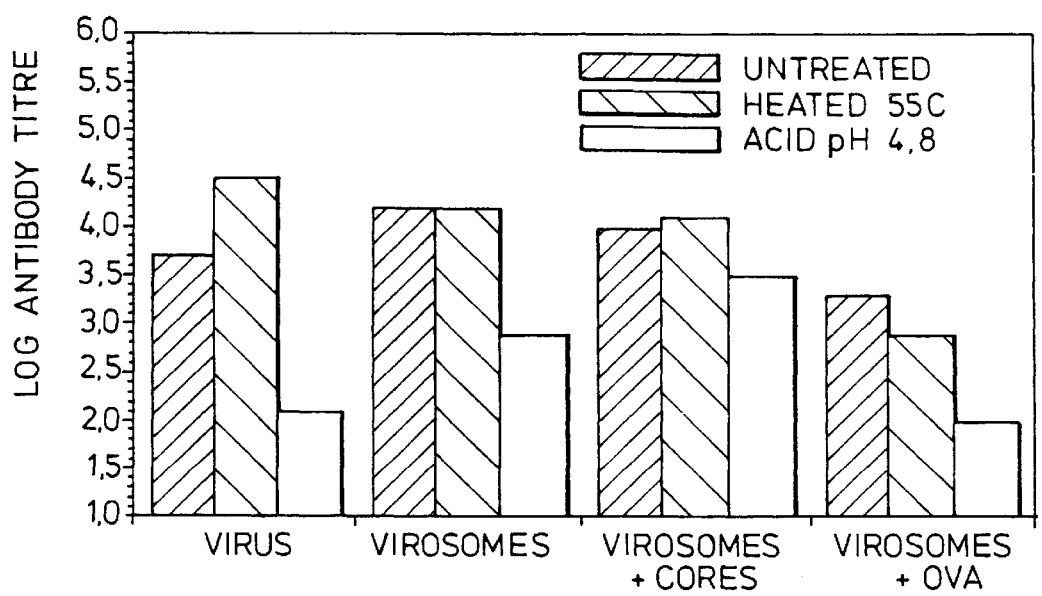
Figure 1C:
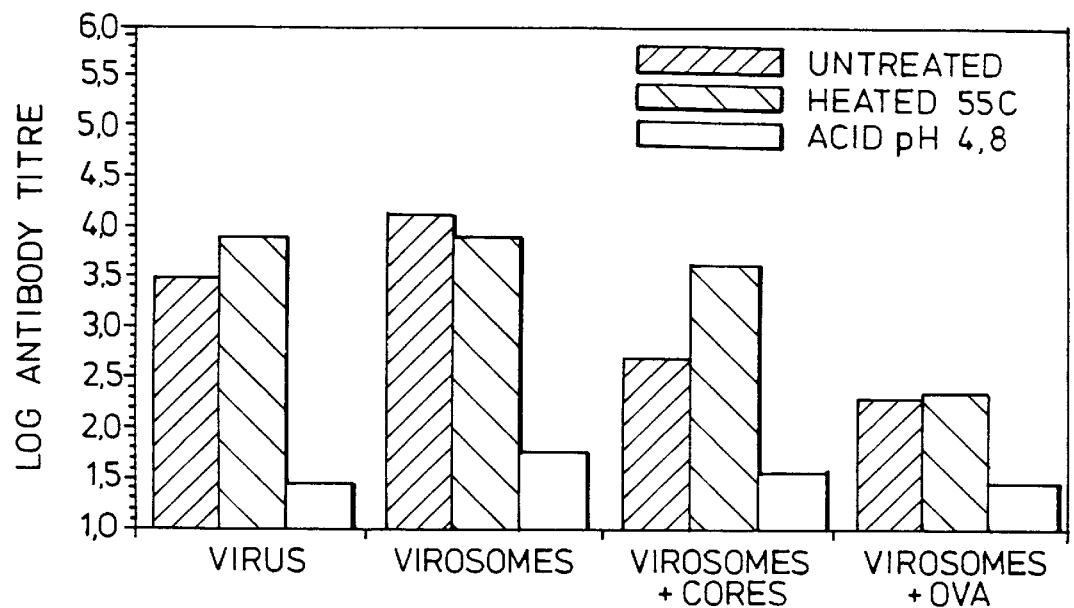

Influenza virus, influenza virosomes, or influenza virosomes containing cores (HBcAg) or ovalbumin were treated with acid (pH 4.8) for 30 min. at 37° C. Acid-treatment of virus or virosomes led to a dramatic reduction in immunogenicity of virus or virosomes given by the intranasal route as assayed by serum ELISA titres against native virus (FIGS. 1A and 2A–5A). This was not due to the fact that acid destroys some of the neutralisation epitopes on haemagglutinin because lower responses were also observed when the sera were tested against SDS-denatured virus (FIG. 1B). In addition, the levels of neutralising antibodies induced were considerably reduced if the inoculum was acid-treated (FIGS. 1C and 2B–5B).

Figure 1D:
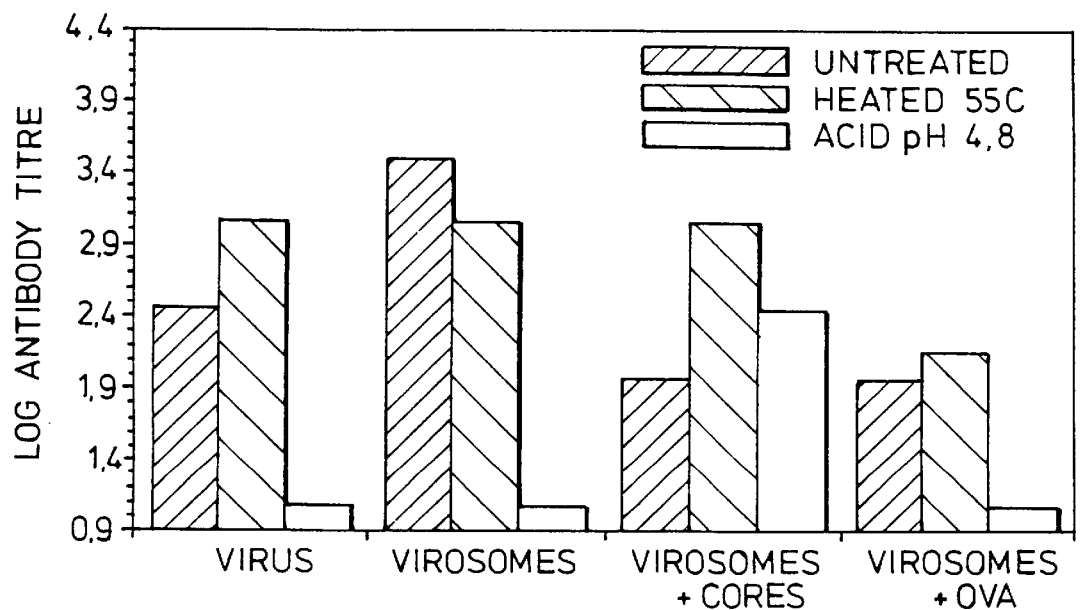
Figure 3A:
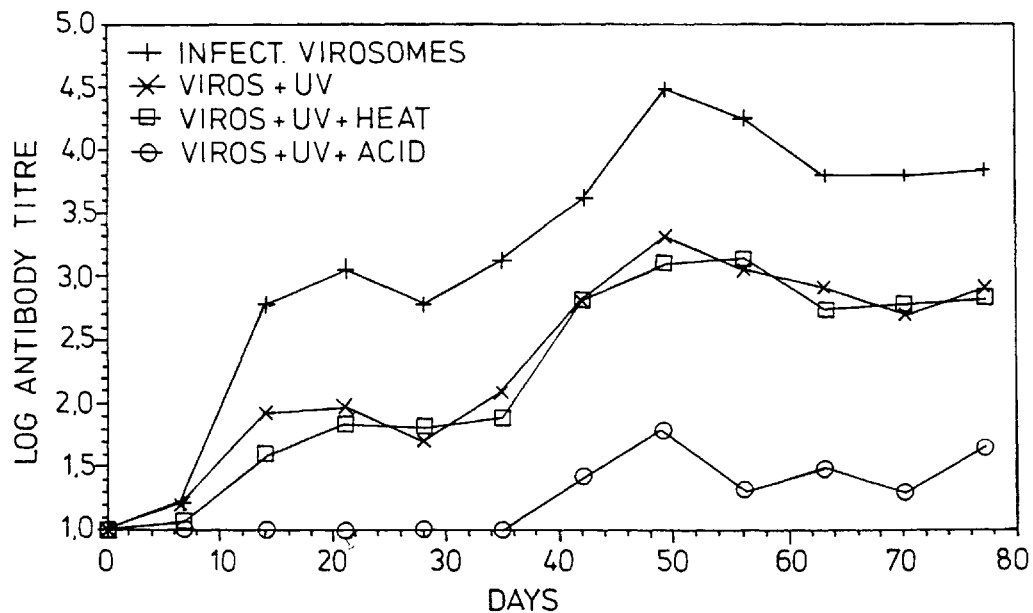
Figure 3B:
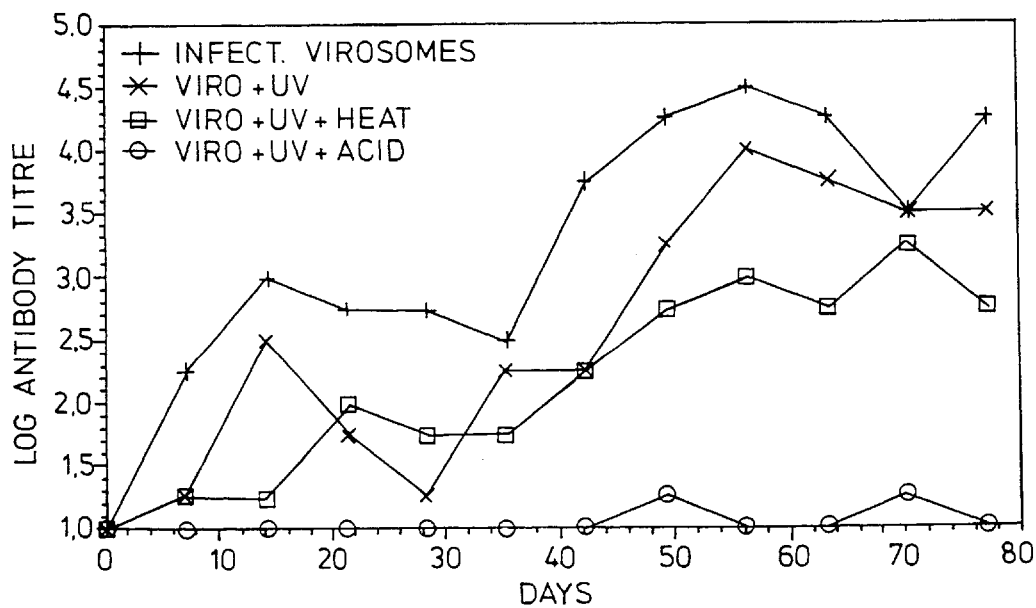
Figure 4A:
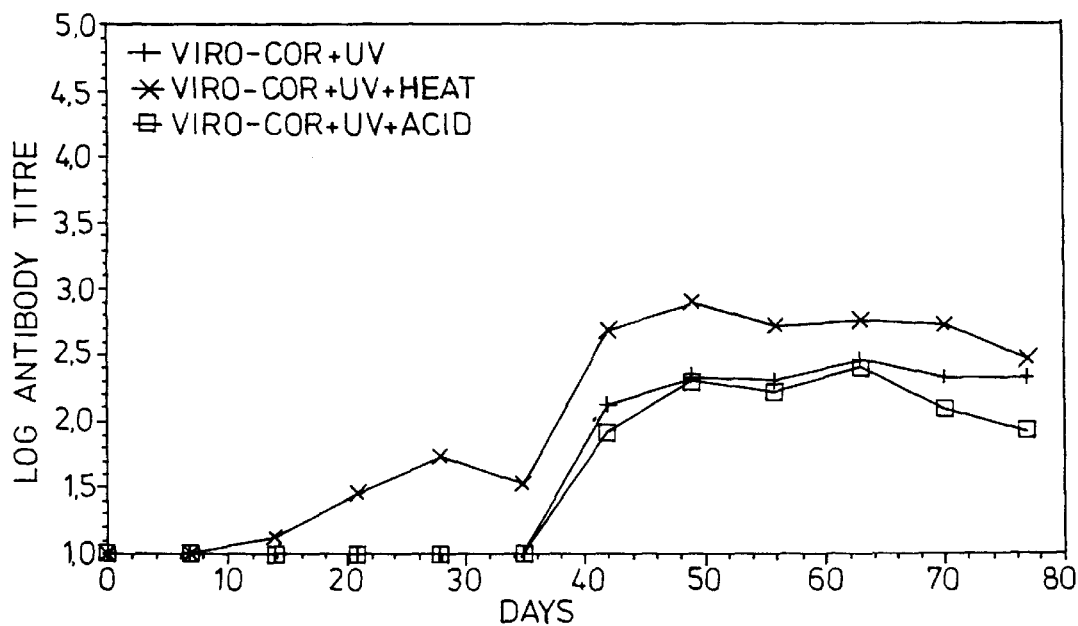

There appeared to be some protection against acid-inactivation of virosomes containing cores but this may be due to insufficient acidification of the boost inoculum (see FIGS. 4A & B). When the response of individual animals was analysed there was a consistent reduction in response if the virus or virosomes were acid treated (FIGS. 6–9). We also looked at the haemagglutination inhibition (HI) activity of the sera (FIG. 1D), which also show a reduction in the titre of antibody stimulated when virosomes were acid treated before inoculation.

Acid-treatment (pH 4.8) of virus abrogates the ability of virus to fuse with cells while virus attachment is unaffected. This is due to the irreversible conformational shift in the conformation of haemagglutinin that normally occurs inside the endosome after uptake of the virus within coated pits. These results suggest that the virus or virosomes must not only bind to the mucosal surfaces but also fuse with the epithelial cells to stimulate optimal responses.

Effect of heating at 55° C. on the immunogenicity of virus

Mice inoculated intranasally with X31 influenza virus heated for 20 min. showed significantly greater serum ELISA, HAI or neutralising antibody titres than mice receiving unheated virus (FIGS. 1A–D). Both the ELISA titres against native virus and the neutralising titres were approaching those observed following immunization with the same dose of infectious virus (FIG. 2). In a further experiment virus was heated for only 8 mins. and again this led to an increase in response following intranasal inoculation (Table 1).

Figure 6A:
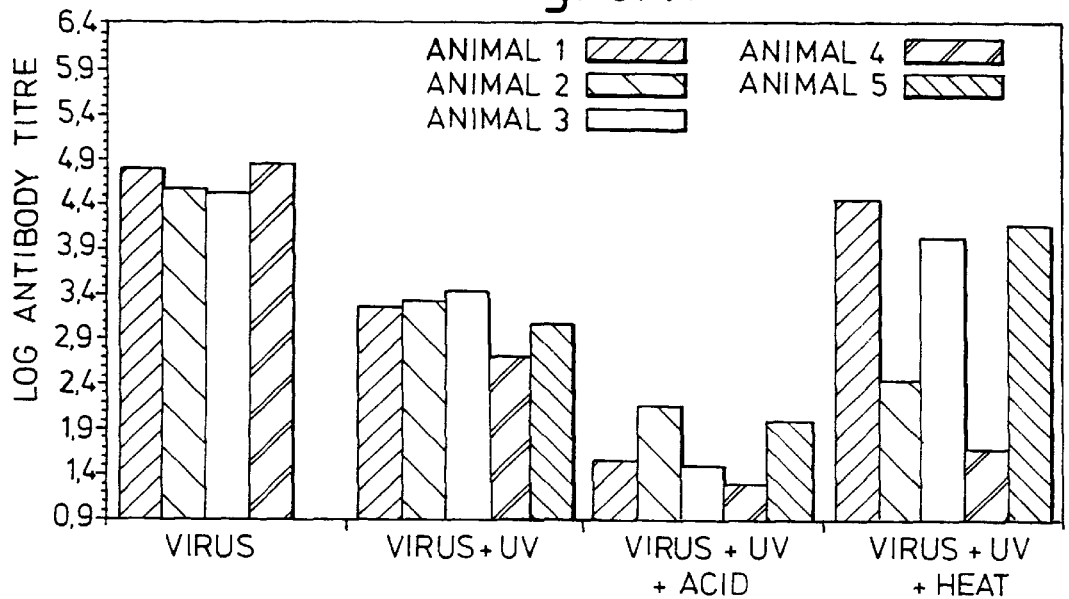
Figure 6B:
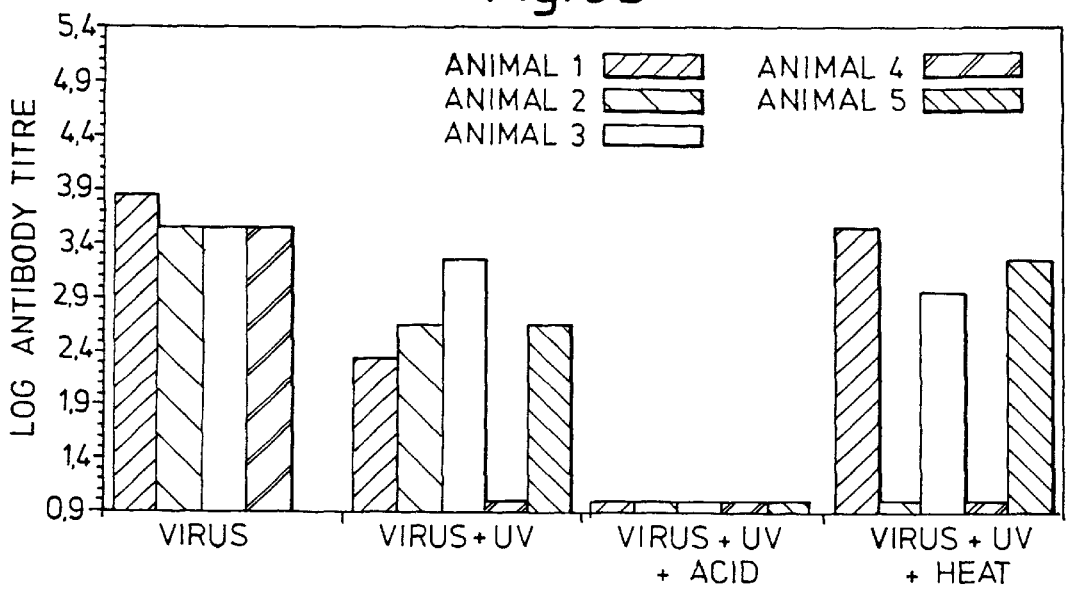

Responses to both the heated or infectious virus were observed at least 21 days before responses to inactivated virus. When the response of individual animals was examined there was an increase in response when the virus was heated and the ELISA titres paralleled the neutralising titres (FIG. 6). There was, however, considerable variation probably due to the efficiency of inoculation.

Effect of heating at 55° C. on the immunogenicity of virosomes

Figure 4B:
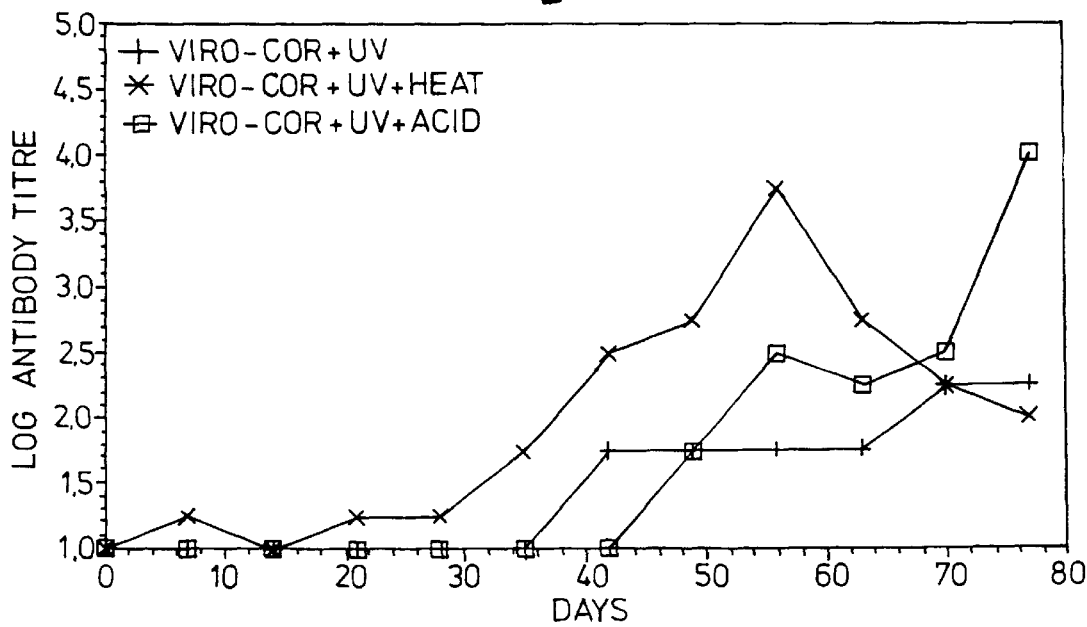
Figure 5A:
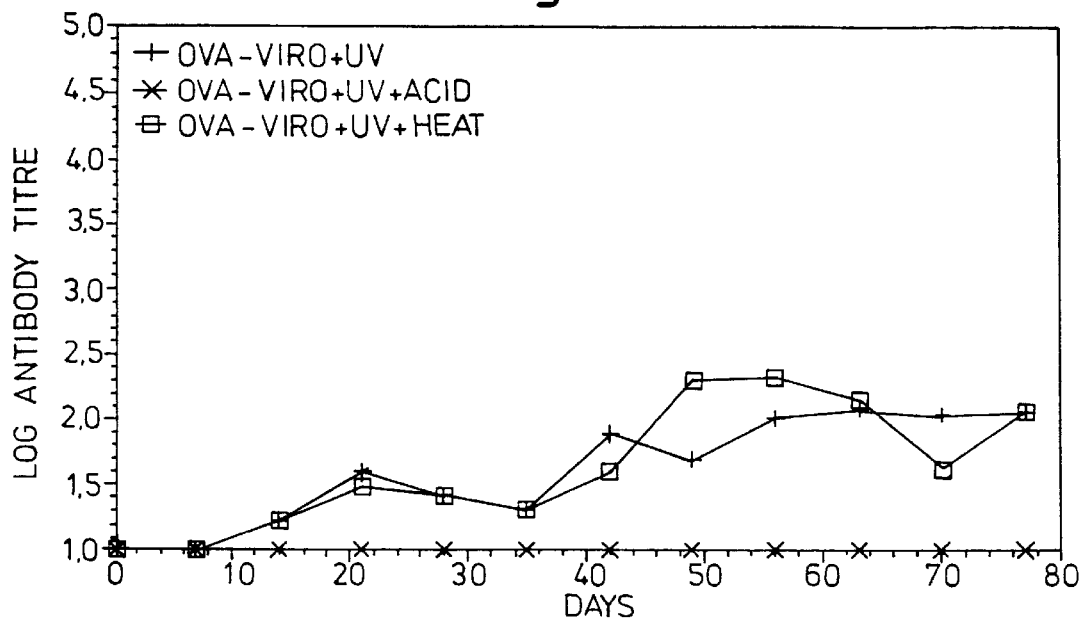
Figure 5B:
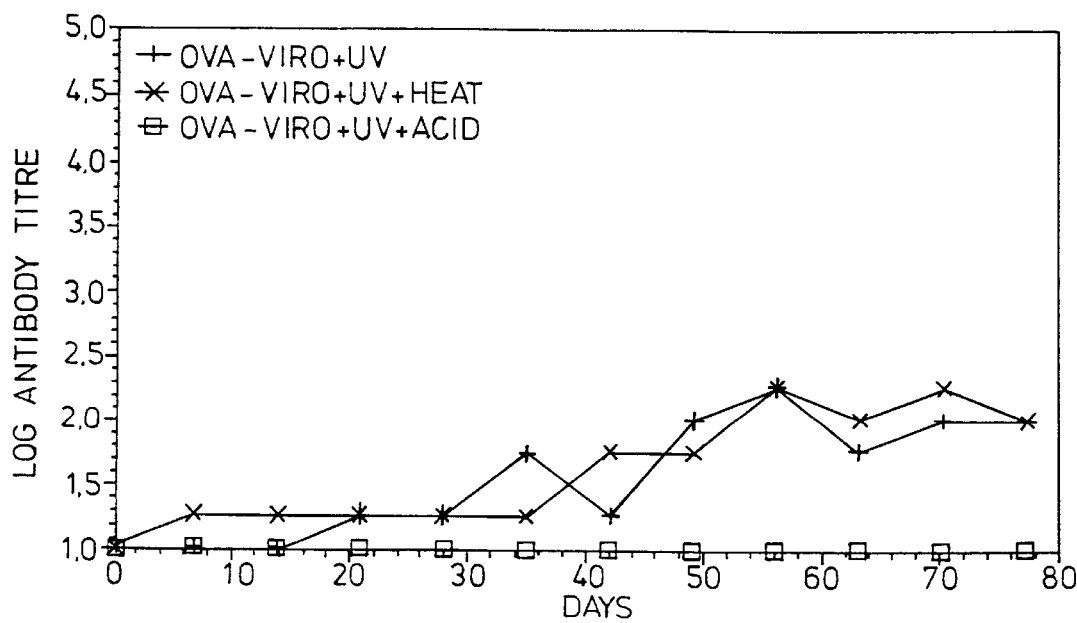
Figure 7A:
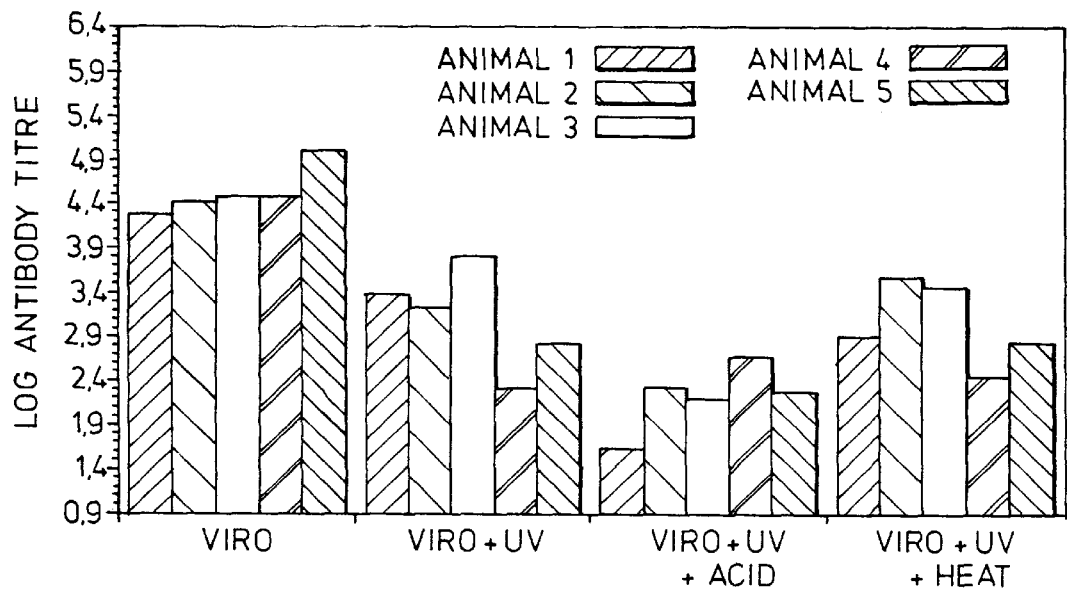
Figure 7B:
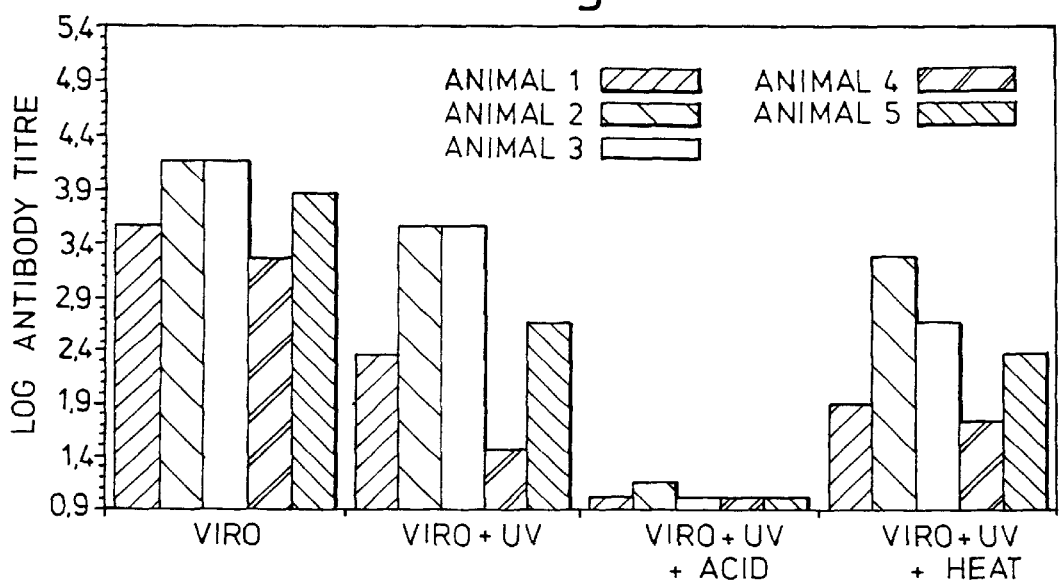
Figure 8A:
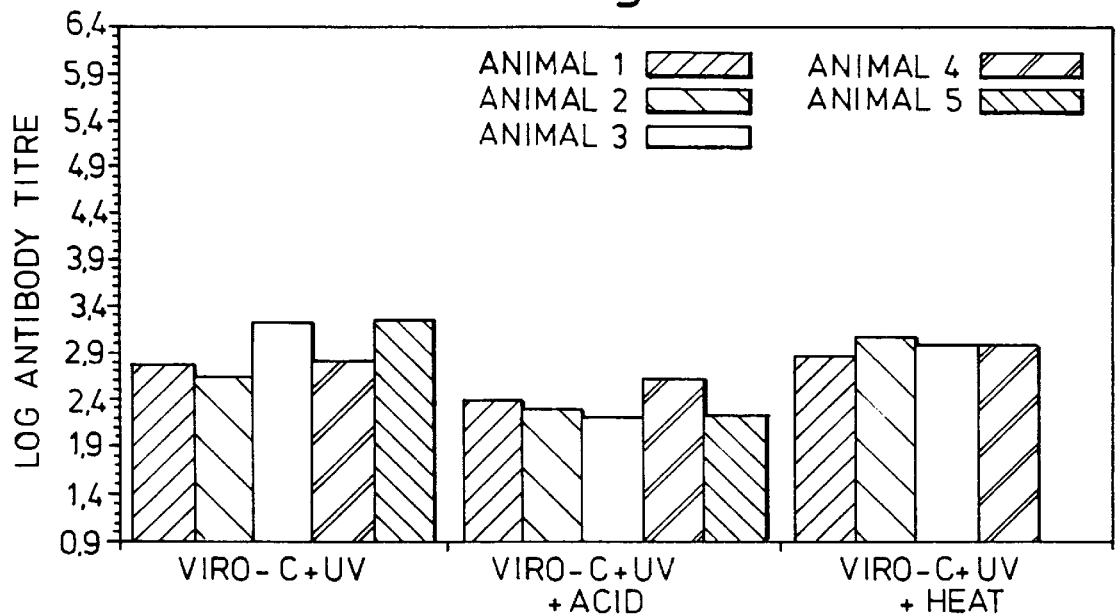
Figure 8B:
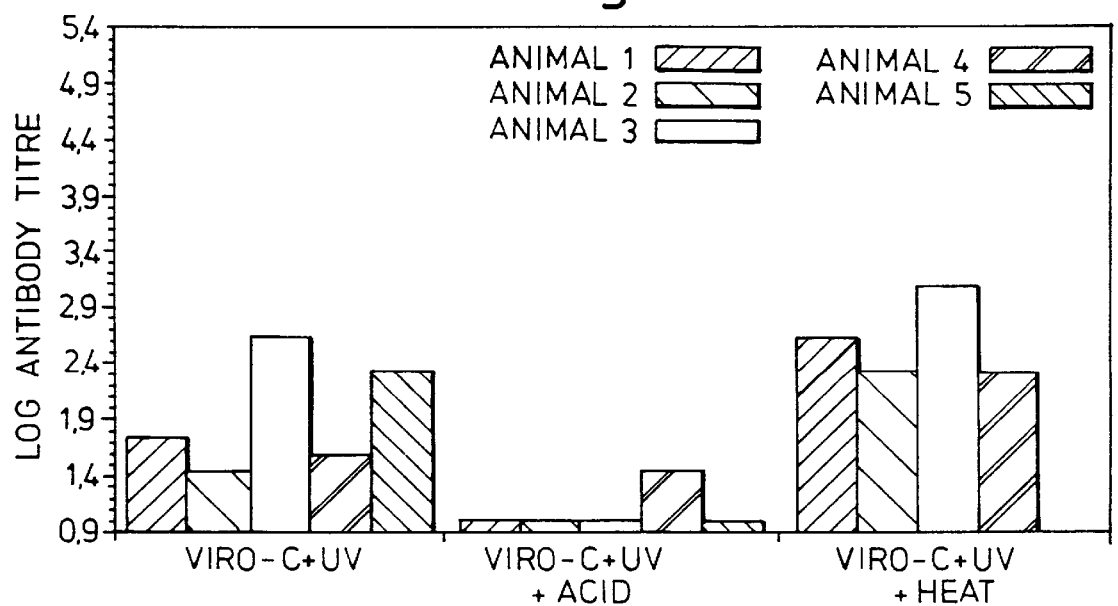
Figure 9A:
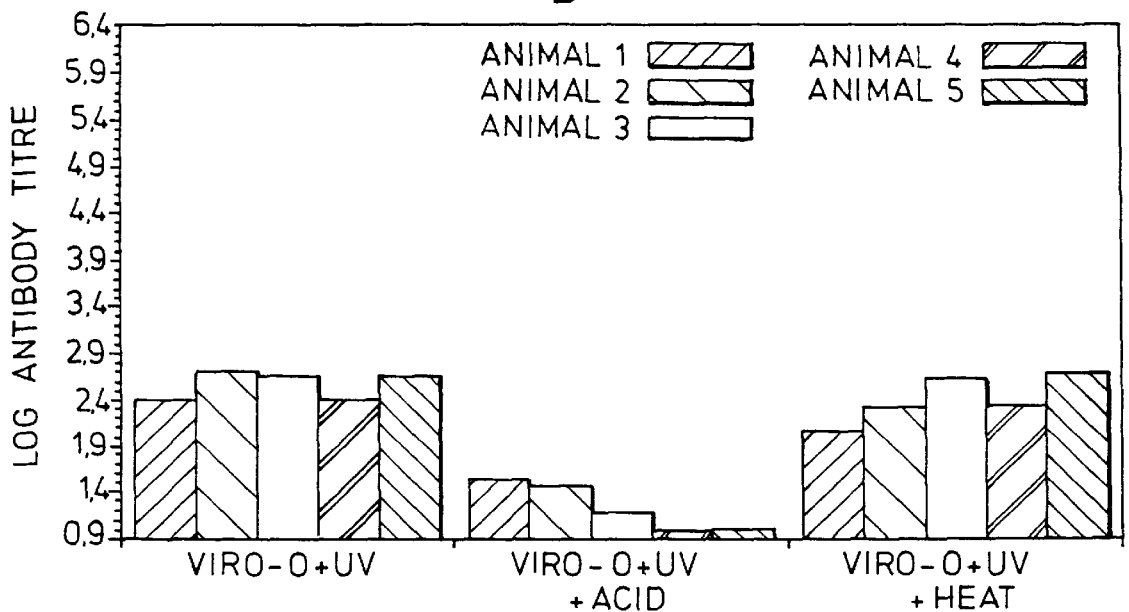
Figure 9B:
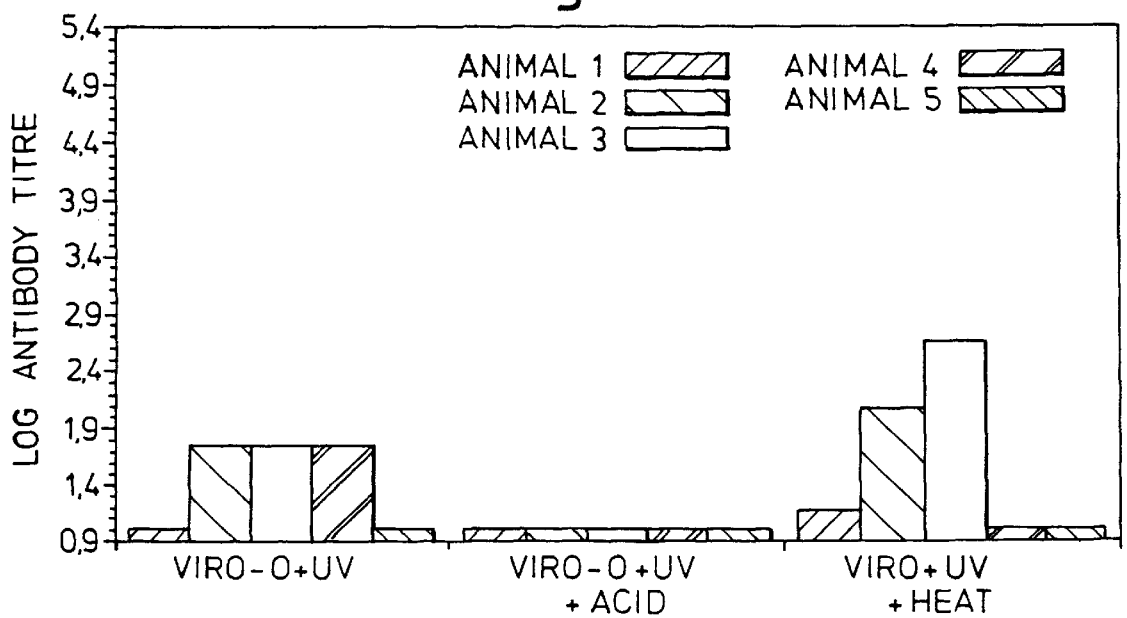

In a preliminary experiment, mice were inoculated intranasally with virosomes, or virosomes containing cores or ovalbumin, that had been heated for 20 min. These heated virosomes stimulated comparable or greater serum ELISA or neutralising titres than mice receiving unheated virosomes (FIGS. 1–5). FIG. 4 shows that uv-inactivated, heated virosomes containing viral cores stimulate a much earlier response than uv-inactivated or acid-treated virosomes. In addition, when the response of individual animals was examined there was little variation within the animal groups (FIG. 7). The neutralisation titres showed greater variation but parallelled the ELISA titres. It should be noted that these virosomes were stored at 4° C., so it is possible that much of the neuraminidase activity was lost.

Figure 10A:
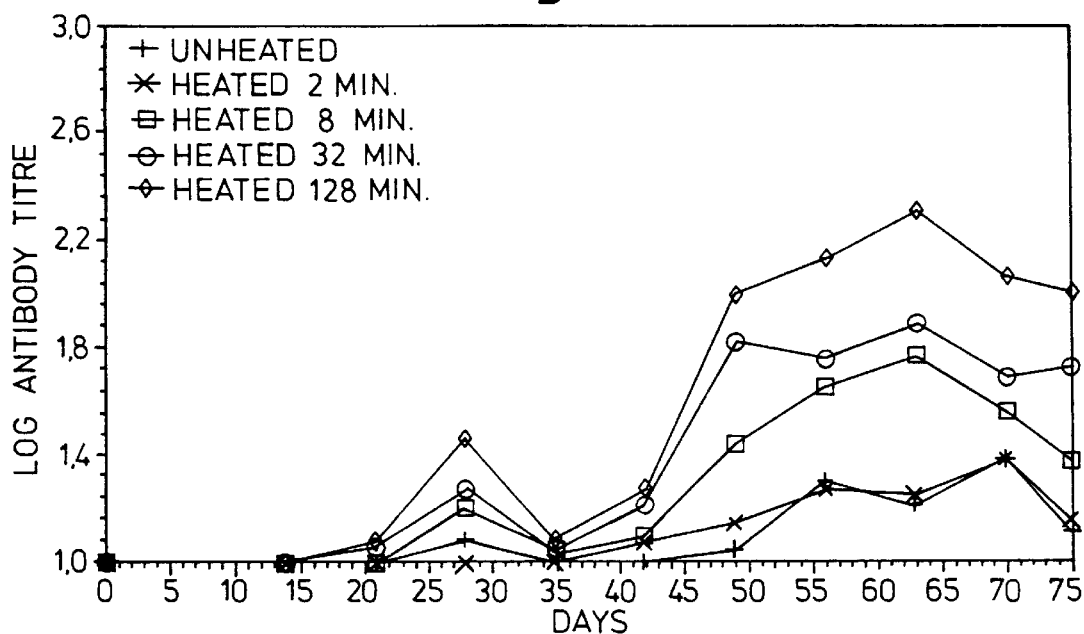
Figure 10B:
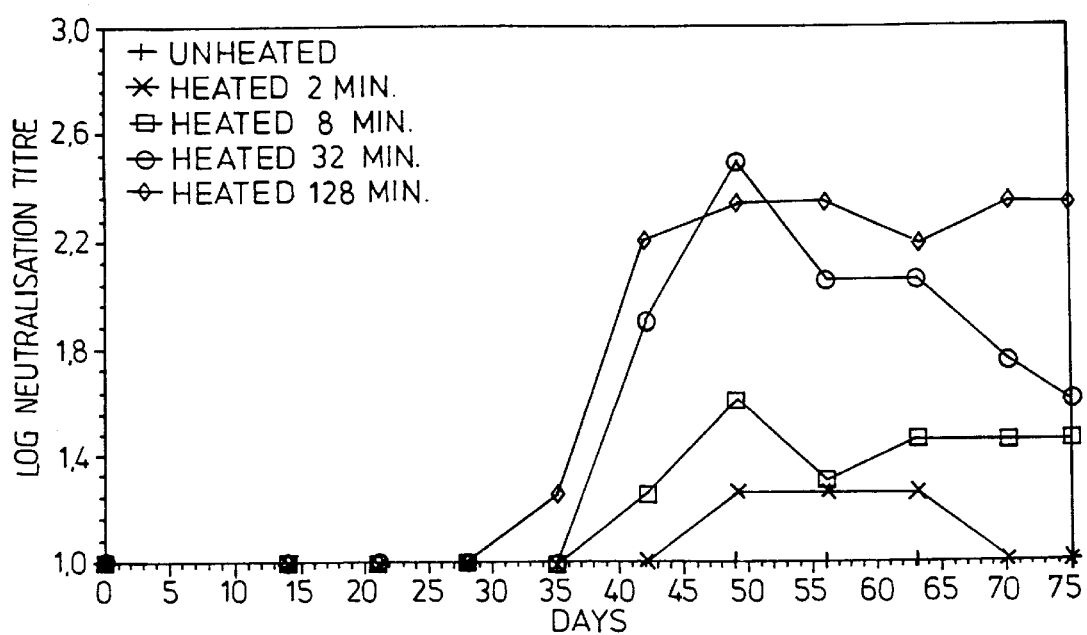
Figure 11A:
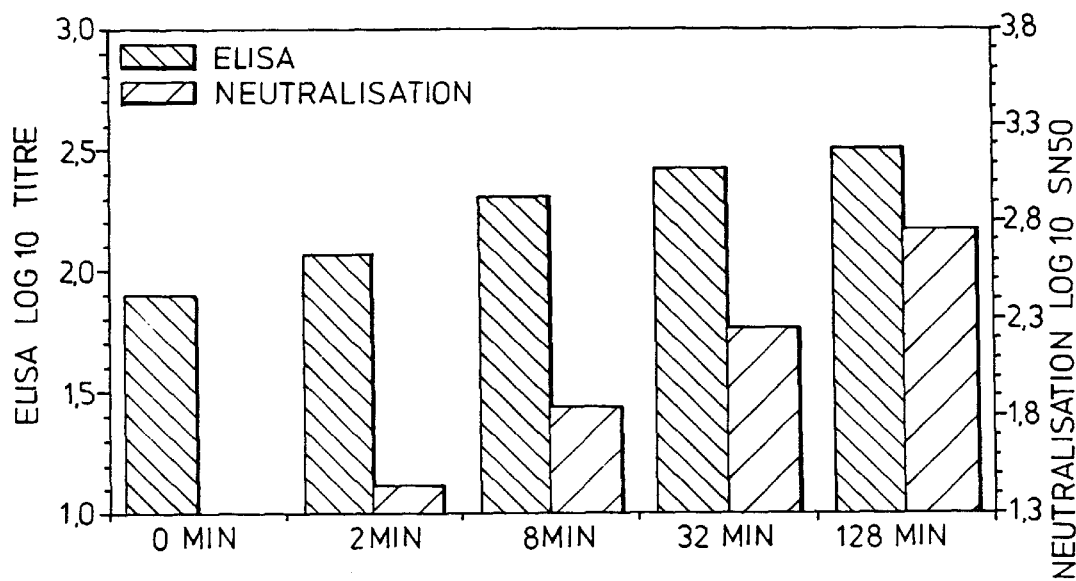
Figure 11B:
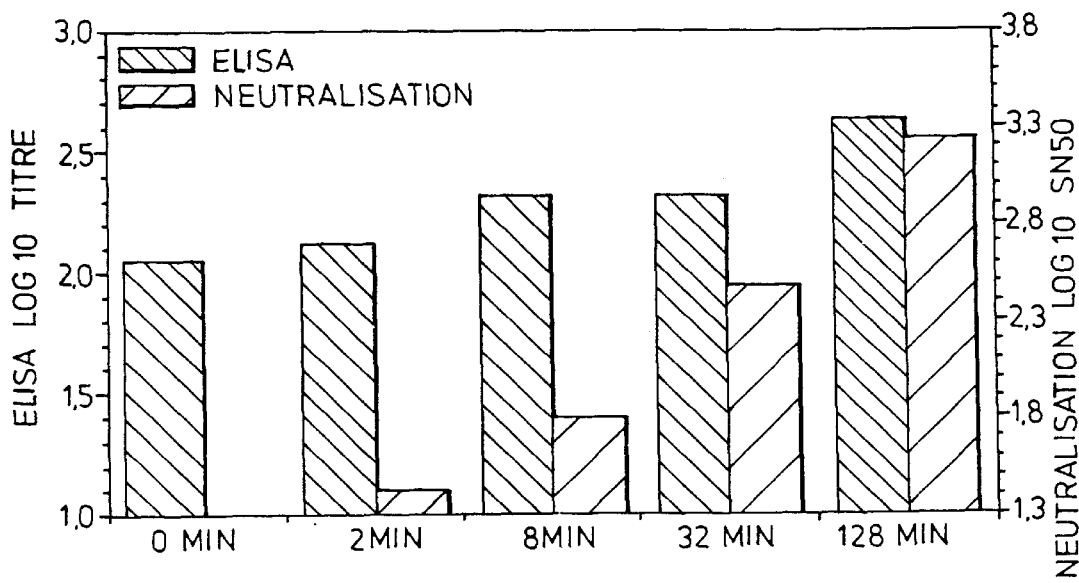
Figure 12A:
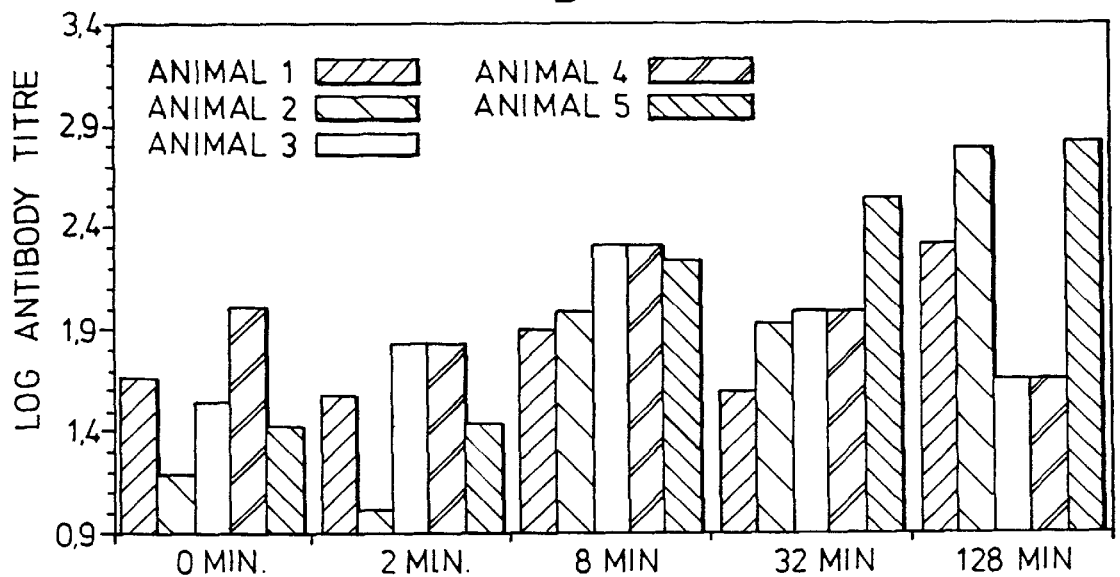
Figure 12B:
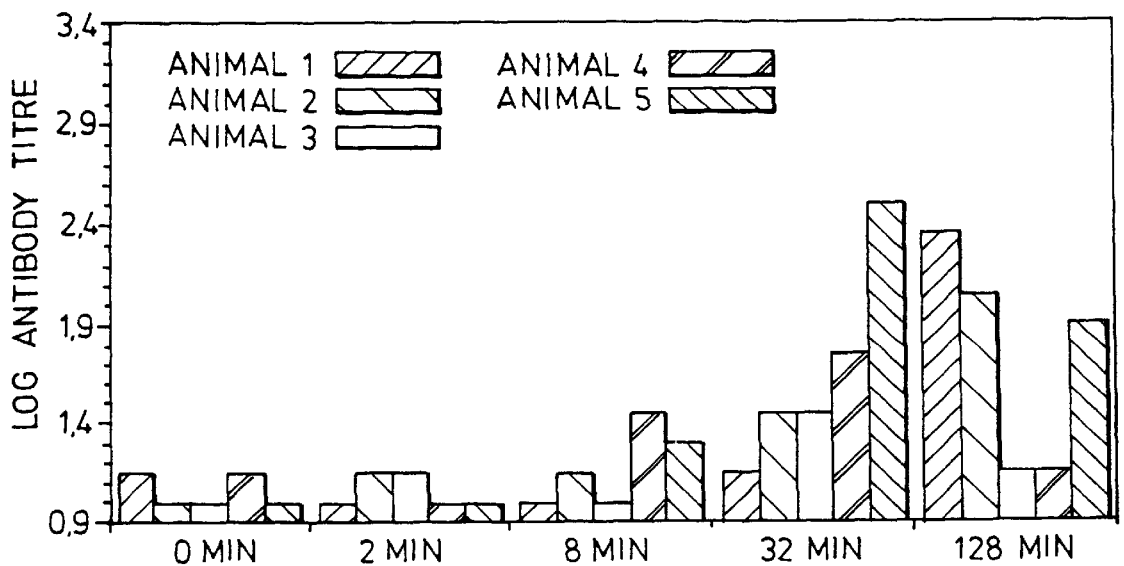

Mice were immunized with fresh virosomes that were stored in 50% glycerol at -20° C. A dramatic increase in immunogenicity was observed if the virosomes were heated for up to 128 mins. (FIGS. 10A and 11, Table 1). The levels of neutralizing antibodies showed a more dramatic increase with increasing periods of heating (FIGS. 10B and 11). Animals immunized with unheated virosomes had undetectable levels of neutralising antibodies suggesting that the high responses observed in the previous experiments with unheated virosomes were due to partial inactivation of neuraminidase activity during storage at 4° C. In addition, when serum from individual mice were analyzed a significant increase in ELISA and neutralising antibody titre was observed in sera from mice receiving virosomes heated for increasing periods of time (Table 2, FIG. 12).

Effect of Specific Inactivation of Neuraminidase on the Immunogenicity of Virosomes Given Intranasally We have carried out an experiment to determine whether the increase in immunogenicity observed with heating of virosomes was due to inhibition of neuraminidase (NA). Thus, the NA in virosomes was specifically inactivated with the neuraminic acid analogue, DDAN. DDAN-treated virosomes stimulated a greater response than untreated virosomes (log titre of 2.2 cf 1.6) showing that inhibition of neuraminidase leads to an increase in immunogenicity of intranasally administered virosomes.

Figure 13:
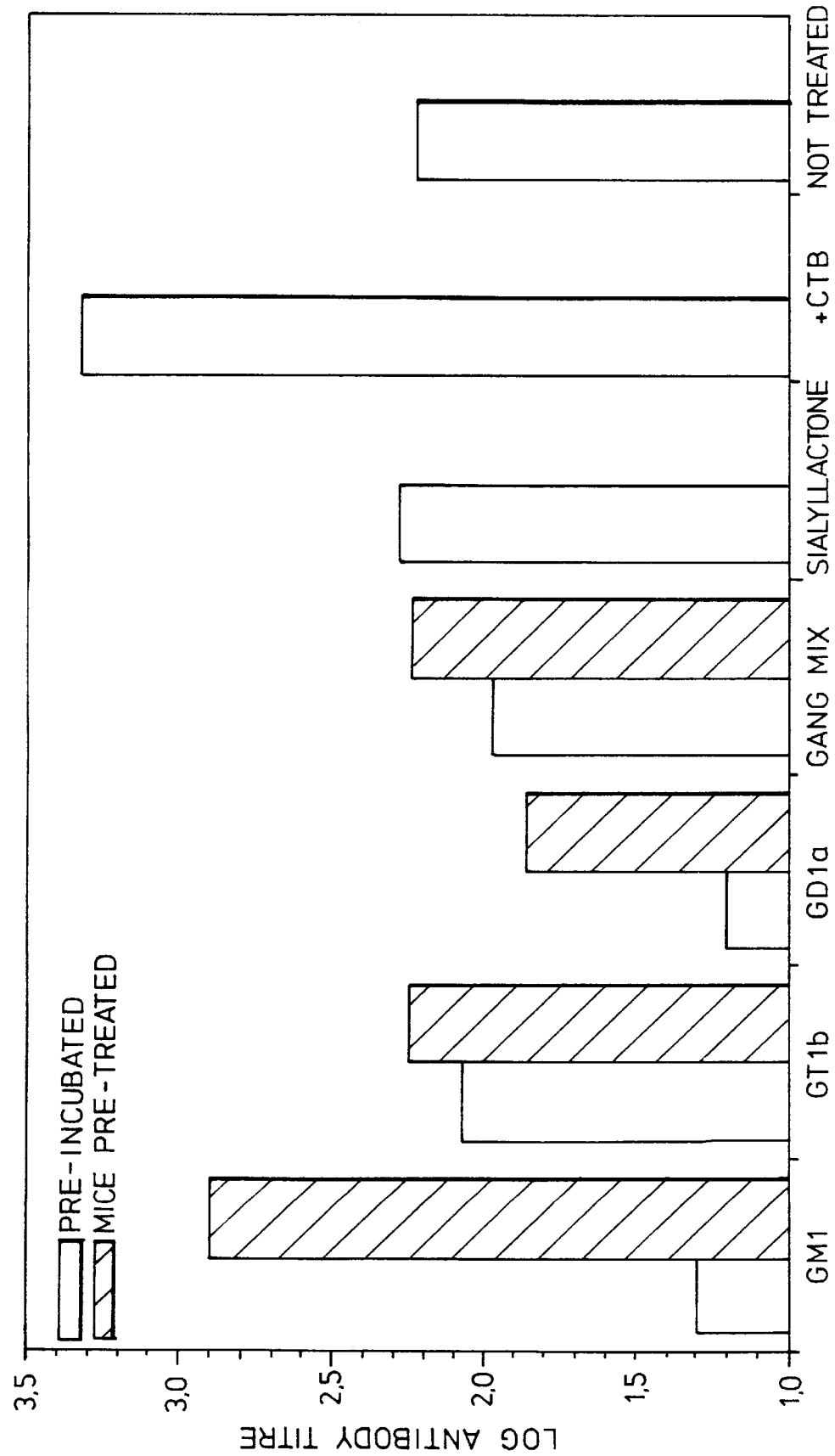

Effect of Specific Blocking of Virosome Attachment by Pre-incubation with Gangliosides on the Immunogenicity of Virosomes given Intranasally In order to study the effect of blocking virosome attachment on the immunogenicity of intranasally administered virosomes we have pre-incubated virosomes in various sialic acid-containing gangliosides. The immunogenicity of influenza virosomes administered intranasally (i.n.) could be partially abrogated by pre-treating the virosomes with GM1 or GD1a gangliosides but not by pre-treating with GT1b or a ganglioside mixture (FIG. 13). Similarly, we have found that the virosome-mediated haemagglutination was partially inhibited only by the GM1 and GB1a gangliosides. These experiments show that binding of virosomes to sialic acid receptors is critical for their immunogenicity.

Effect of ore-treating mice with gangliosides on the response of mice to virosomes given intranasally We have studied the effect on the response to virosomes of increasing the viral receptors on the respiratory mucosal surfaces through intranasal pre-treatment of mice with various gangliosides (FIG. 13). Pre-treatment with GM1 ganglioside but not GD1a GT1b or a ganglioside mixture led to an increase in response presumably because of an increase in density of receptors or replacement with higher affinity receptors on the mucosal surfaces facilitating greater binding and uptake of the virosomes.

Effect of Specific Blocking of Virosome Attachment by Pre-incubation with Neutralising Monoclonal Antibodies on the Immunogenicity of Virosomes Given Intranasally Pre-incubation of virosomes with a neutralising monoclonal antibody (either whole or Fab fragments) completely inhibited haemagglutination. However, the immunogenicity of the virosomes was unaffected by prior incubation of virosomes in whole antibody or Fab fragments or i.n. inoculation of Fab fragments 2 hours after inoculation with untreated virosomes. This result is surprising and may indicate that some neutralising antibodies do not prevent virus binding or entry into mucosal epithelia but some later event (e.g. secondary uncoating). Studying the fate of antibody-treated virus or virosomes should provide some insight into the mechanisms of humoral immunity in the respiratory tract. Moreover, with regards intranasal vaccination of humans, it is encouraging if the presence of local neutralising antibody fails to reduce the immunogenicity of intranasally-administered virosomes.

Effect of Administering the B-subunit of Cholera Toxin (CT-B) Intranasally Together with Virosomes on the Immunogenicity of the Virosomes We investigated whether CTB could enhance the responses to virosomes administered intranasally. FIG. 13 shows that there was a dramatic increase (10-fold) in response to the virosomes when given with CTB). We have repeated this experiment using heated virosomes which we would expect to be much more immunogenic.

Protection against Challenge

All the animals receiving intranasal immunisations of virus or virosomes have been challenged with live virus and the lungs were removed 2 days later. Preliminary challenge lung titres indicate that animals immunised with virus or virosomes that were not acid-treated were completely protected against infection.

TABLE 1

INTRANASAL IMMUNISATION OF BALB/C MICE WITH INFLUENZA VIROSOMES
Effect of heating at 55° C. on immunogenicity of virosomes

| Group | Antigen | Heat | Dose | ELISA TITRE (OD) |
|---|---|---|---|---|
| 63A | VIROSOMES | Not heated | 3 μg | 1.90 (0.25) |
| 63B | VIROSOMES | heated 2 min | 3 μg | 2.02 (0.25) |
| 63C | VIROSOMES | heated 8 min | 3 μg | 2.52 (0.43) |
| 63D | VIROSOMES | heated 32 min | 3 μg | 2.80 (0.54) |
| 63E | VIROSOMES | heated 128 min | 3 μg | 3.09 (0.64) |
| 63F | VIRUS | Not heated | 3 μg | 2.44 (0.44) |
| 63G | VIRUS | heated 8 min | 3 μg | 2.87 (0.77) |
| 63H | in. PBS | control | | <1.50 (0.17) |

Bleed tested: 23/2/90 - 4 weeks after primary immunisation

TABLE 2

INTRANASAL IMMUNISATION OF BALB/C MICE WITH INFLUENZA VIROSOMES - RESPONSE OF INDIVIDUAL MICE
Effect of heating at 55° C. on Immunogenicity

| | | | | ELISA TITRES | | MEAN TITRE | |
|---|---|---|---|---|---|---|---|
| Group | Antigen | Heat | Animal | NV | DV | NV | DV |
| 63A | VIROSOMES | Not heated | G | 1.21 | 1.23 | | |
| | | | Y | 1.98 | 1.89 | | |
| | | | M | 1.26 | 1.14 | 1.84 | 1.44 |
| | | | W | 1.48 | 1.23 | | |
| | | | R | 1.31 | 1.10 | | |
| 63B | VIROSOMES | heated 2 min | M | <1.00 | <1.00 | | |
| | | | W | 1.38 | 1.02 | | |
| | | | G | 2.02 | 1.38 | 1.64 | 1.24 |
| | | | R | 1.24 | 1.22 | | |
| | | | Y | 1.78 | 1.42 | | |
| 63C | VIROSOMES | heated 8 min | R | 2.26 | 1.99 | | |
| | | | Y | 1.21 | 1.06 | | |
| | | | G | 1.72 | 1.81 | 1.95 | 1.69 |
| | | | W | 1.86 | 1.80 | | |
| | | | M | 2.12 | 1.13 | | |
| 63D | VIROSOMES | heated 32 min | M | 2.33 | 1.75 | | |
| | | | Y | 2.22 | 2.28 | | |
| | | | R | 1.78 | 2.16 | 2.12 | 2.04 |
| | | | G | 2.25 | 2.19 | | |
| | | | W | 1.65 | 1.07 | | |
| 63E | VIROSOMES | heated 128 min | R | 2.33 | 2.33 | | |
| | | | Y | 2.59 | 2.24 | | |
| | | | M | 1.84 | 1.51 | 2.31 | 2.46 |
| | | | W | 1.88 | 1.48 | | |
| | | | G | 2.47 | 2.99 | | |

Bleed tested: 30/3/90 - 4 weeks after second immunisation.

Dose response study of virosomes administered intranasally

We have studied the response to a range of doses of virosomes administered intranasally. These virosomes were unheated and fresh so the antibody responses are relatively low. A clear dose response effect was observed with the minimal immunogenic dose being 1 μg (FIG. 14). We have

I claim:

1. Liposomes which have present on their surface a polypeptide which binds to a mucosal cell surface of a human or animal and which renders the liposomes fusogenic with the mucosal cell surface, and which are free of neuraminidase enzymatic activity.

2. Liposomes according to claim 1, in which the polypeptide is a haemagglutinin of a myxovirus.

3. Liposomes according to claim 2, in which the myxovirus is selected from the group consisting of influenza, mumps and measles virus.

4. Liposomes according to claim 1, in which the polypeptide is a bacterial adhesion polypeptide.

5. Liposomes according to claim 1, which encapsulate a physiologically active substance.

6. Liposomes according to claim 5, wherein the substance is selected from the group consisting of peptides, proteins and adjuvants.

7. A process for the preparation of liposomes according to claim 1, which process comprises forming liposomes which have present on their surfaces the said polypeptide and which are free of neuraminidase enzymatic activity.

8. A process according to claim 7, which comprises:
 (a) removing the viral genome and internal viral protein or proteins;
 (b) forming liposomes in the presence of remaining viral material; and
 (c) inactivating the neuraminidase present in the thus-formed liposomes.

9. A process according to claim 8, wherein the neuraminidase is inactivated by heat or by incubation with neuraminidase inhibitor.

10. A process according to claim 9, in which the inactivation is achieved by heating to a temperature from 50 to 60° C., or by incubation with 2,3-dehydro-2-deoxy-N-acetylneuraminic acid.

11. A process according to claim 7, wherein liposomes are formed using the said polypeptide which is a recombinant polypeptide.

12. A pharmaceutical composition which comprises liposomes according to claim 1 in association with a pharmaceutically acceptable carrier or diluent.

13. A composition according to claim 12 which is in aerosol form.

\* \* \* \* \*

UNITED STATES PATENT AND TRADEMARK OFFICE
CERTIFICATE OF CORRECTION

PATENT NO.    : 5,985,318
DATED         : November 16, 1999
INVENTOR(S)   : Ford, Martin J.

It is certified that error appears in the above-identified patent and that said Letters Patent is hereby corrected as shown below:

<u>Title page,</u>
Change,
"[73] Assignee:     Burroughs Wellcome Co., Research Triangle Park, N.C."

to read as:

-- [73] Assignee:     Medeva Pharma Limited, Leatherhead, Surrey, United Kingdom --

Signed and Sealed this

Twenty-ninth Day of July, 2003

JAMES E. ROGAN
*Director of the United States Patent and Trademark Office*